US009326827B2

(12) United States Patent
Estwick et al.

(10) Patent No.: US 9,326,827 B2
(45) Date of Patent: May 3, 2016

(54) STERILE SURGICAL HEADLIGHT APERTURE ADJUSTING DEVICE

(71) Applicant: SteriClip LLC, Newport Coast, CA (US)

(72) Inventors: Gareth Estwick, Newport Coast, CA (US); Rian Rifkin, Newport Beach, CA (US)

(73) Assignee: SurgiRight LLC, Vancouver, WA (US)

( * ) Notice: Subject to any disclaimer, the term of this patent is extended or adjusted under 35 U.S.C. 154(b) by 340 days.

(21) Appl. No.: 13/851,087

(22) Filed: Mar. 26, 2013

(65) Prior Publication Data

US 2014/0293589 A1 Oct. 2, 2014

(51) Int. Cl.
*A61B 1/06* (2006.01)
*A61B 19/00* (2006.01)

(52) U.S. Cl.
CPC .............. *A61B 19/5202* (2013.01); *A61B 19/26* (2013.01); *A61B 2019/262* (2013.01)

(58) Field of Classification Search
CPC .................. A61B 2019/262; A61B 2019/267; A61B 19/5202; A61B 19/26; A61B 1/06; F21F 21/084; F21V 21/084; F21L 15/14
USPC .......................... 81/120, 176.2, 176.15, 176.1
See application file for complete search history.

(56) References Cited

U.S. PATENT DOCUMENTS

| | | | |
|---|---|---|---|
| 3,557,791 A * | 1/1971 | Duffy | 606/1 |
| 4,916,597 A | 4/1990 | Hallings et al. | |
| 4,974,288 A | 12/1990 | Reasner | |
| D373,433 S | 9/1996 | Feinbloom | |
| 6,086,228 A * | 7/2000 | McGowan et al. | 362/396 |
| 6,224,227 B1 | 5/2001 | Klootz | |
| 6,745,648 B2 * | 6/2004 | Stier | 81/119 |
| 6,905,223 B2 * | 6/2005 | Halasz | 362/197 |
| 7,210,810 B1 | 5/2007 | Iversen et al. | |
| 7,757,352 B2 | 7/2010 | Halamish | |
| 8,348,448 B2 | 1/2013 | Orozco et al. | |
| 2012/0120635 A1* | 5/2012 | Strong et al. | 362/105 |

* cited by examiner

*Primary Examiner* — Eduardo C Robert
*Assistant Examiner* — Julianna N Harvey
(74) *Attorney, Agent, or Firm* — Craig A. Crandall, APC

(57) ABSTRACT

The present invention relates to medical devices, and more specifically, the present invention relates to a medical device that allows a surgeon to personally adjust the aperture of the light beam being projected from his or her surgical headlight during surgery, as often as necessary and without compromising the sterile field.

4 Claims, 5 Drawing Sheets

STERILE SURGICAL HEADLIGHT APERTURE ADJUSTING DEVICE

BACKGROUND OF THE INVENTION

The use of surgical headlights to provide a spotlight beam of intense light coincident with the wearer's line of sight, independent from overhead and/or ambient lighting, is well established in the art. Surgical headlight systems typically include a headlight assembly mounted to a surgical headgear at the wearer's forehead at a location approximately between the wearer's eyes. A typical headlight assembly comprises an assembly of optic elements and a light source (xenon or halogen) and can receive an emitting end of a fiber optic cable and then focus and direct the light from the cable into a beam aimed forward of the wearer. Alternatively, the headlight assembly may comprise an LED (light emitting diode) mounted in its housing and used as the light source. The LED light source is connected by a cable to a power supply.

Various models of commercially-available surgical headgear comprise a headlight assembly which comprises an aperture adjusting component (e.g., an aperture adjusting dial) which is manipulated by the wearer to adjust the aperture of the light beam. Unfortunately, these aperture adjusting components cannot be fully utilized for their intended purpose due to lack of sterility and associated risk factors. Specifically, the headgear itself, including the headlight assembly and aperture adjusting component, is not sterile. As such, the surgeon typically adjusts the aperture adjusting component to a particular setting prior to entering the sterile field and then is unable to personally manipulate the non-sterile component to re-adjust the aperture after entering the sterile field because he or she would compromise the sterile field. So in order for the aperture to be adjusted, a non-sterile assistant reaches into the sterile field to adjust the component; or alternatively, the surgeon may instinctively attempt to adjust the component using some other sterile tool (e.g., forceps) not designed to adjust the component, and then discard the tool. Clearly, such procedures are not efficient, slow down the operation, and introduce an unnecessary sterility risk factor. This limitation discourages the surgeon from adjusting the aperture in situations where he or she might otherwise have done so but for the inconvenience and risk.

There thus clearly exists a need in all operating room settings to provide a more efficient and safe procedure that would allow the surgeon to personally adjust the aperture adjusting component on his or her surgical headlight without the assistance of another and without compromising the sterile field.

SUMMARY OF THE INVENTION

The present invention relates to medical devices, and more specifically, the present invention relates to a medical device that allows a surgeon to personally adjust the aperture of the light beam being projected from his or her surgical headlight during surgery, as often as necessary, and without compromising the sterile field.

In various embodiments, the medical device comprises a sterile, disposable, single-use aperture adjusting device comprising a handle having a proximate end and an operation portion at its distal end; wherein said operation portion is specifically engineered to engage and hold by friction an aperture adjusting component positioned on a surgical headlight assembly; wherein the handle serves to facilitate the engagement of the device to the aperture adjusting component; wherein engagement of said aperture adjusting device to said aperture adjusting component allows a user to use said handle to manipulate the aperture adjusting component, thereby adjusting the aperture of the light beam being projected from said headlight during surgery. Because the handle of the aperture adjusting device is sterile, the surgeon can manipulate the handle as often as necessary, without the assistance of others, and without compromising the sterile field.

According to one embodiment of the invention, the aperture adjusting component of the surgical headlight assembly comprises an aperture adjusting dial, and the sterile aperture adjusting device comprises a thin rod-shaped handle having a proximate end and having an operation portion comprising a U-shaped collar at its distal end. The U-shaped collar's interior is specifically engineered to engage the outside surface of the aperture adjusting dial, thus allowing for the aperture adjusting device to engage and hold by friction the aperture adjusting dial. The engagement of the device to the dial is facilitated by use of the sterile handle and then allows the user to use the sterile handle to manipulate the dial to adjust the aperture of the light beam being projected from the surgical headlight as often as necessary during surgery, without compromising the sterile field.

According to a further aspect of the present invention, a method of adjusting the aperture of the light beam being projected from a surgical headlight assembly secured to the head of a surgeon during surgery is provided. The method includes: removal of a sterile aperture adjusting device of the invention from its packaging by a medical professional or surgeons assistant in the sterile field, without compromising its sterility; use of the handle of said aperture adjusting device by the surgeon to engage said device to an aperture adjusting component positioned on said surgical headlight assembly; and use of said handle by the surgeon to manipulate said adjusting component to adjust the aperture of the projected light beam during surgery as often as necessary, without compromising the sterile field. After the surgical procedure has been completed, the aperture adjusting device is disengaged from the aperture dial by the surgeon (or other personnel) using the handle of the device to pull the device away from the headlight assembly using gentle force. The aperture adjusting device can then be properly disposed as medical waste.

The present invention will be further exemplified and described in detail by FIGS. 1-5 and the disclosure below. The drawings are not intended to limit the scope of the invention but only to clarify and exemplify certain embodiments of it.

DETAILED DESCRIPTION OF THE PREFERRED EMBODIMENTS

Importantly, the aperture adjusting devices of the invention will be manufactured using a material that possesses two key properties: 1) a material that can be sterilized using FDA approved sterilization techniques; and 2) a material that possesses excellent memory properties ("resiliency") allowing it to temporarily expand and contract back to its original shape, such that it can engage and hold by friction the aperture adjusting component, and then be disengaged from said component by gentle force. Any plastic or metal material possessing such properties can be used in the manufacturing of the aperture adjusting devices of the invention. Many such modern plastics and/or metals are well known to those of ordinary skill in the art. The aperture adjusting devices of the invention can be manufactured as a one piece device or as multiple components which are assembled just prior to use. Methods of manufacturing the devices of the present invention are well known and understood by those of ordinary skill in the art.

The handle may comprise various alternative forms (e.g., rod-shaped, square, flat). In certain embodiments, the handle portion will be between 2.0 and 4.0 inches in length. The handle is used to facilitate the engagement of the operation portion at its distal end to the aperture adjusting component located on the surgical headlight assembly. Alternatively, the handle will itself engage an operation portion which has already been engaged to the aperture adjusting component on the surgical headlight. The handle is then used to manipulate the aperture adjusting component to adjust the aperture of the light beam being projected from the surgical headlight assembly during surgery. Importantly, the handle is sterile and only removed from its packaging in the sterile field. This allows the user to use the handle as often as necessary without compromising the sterile field.

Figure 4:
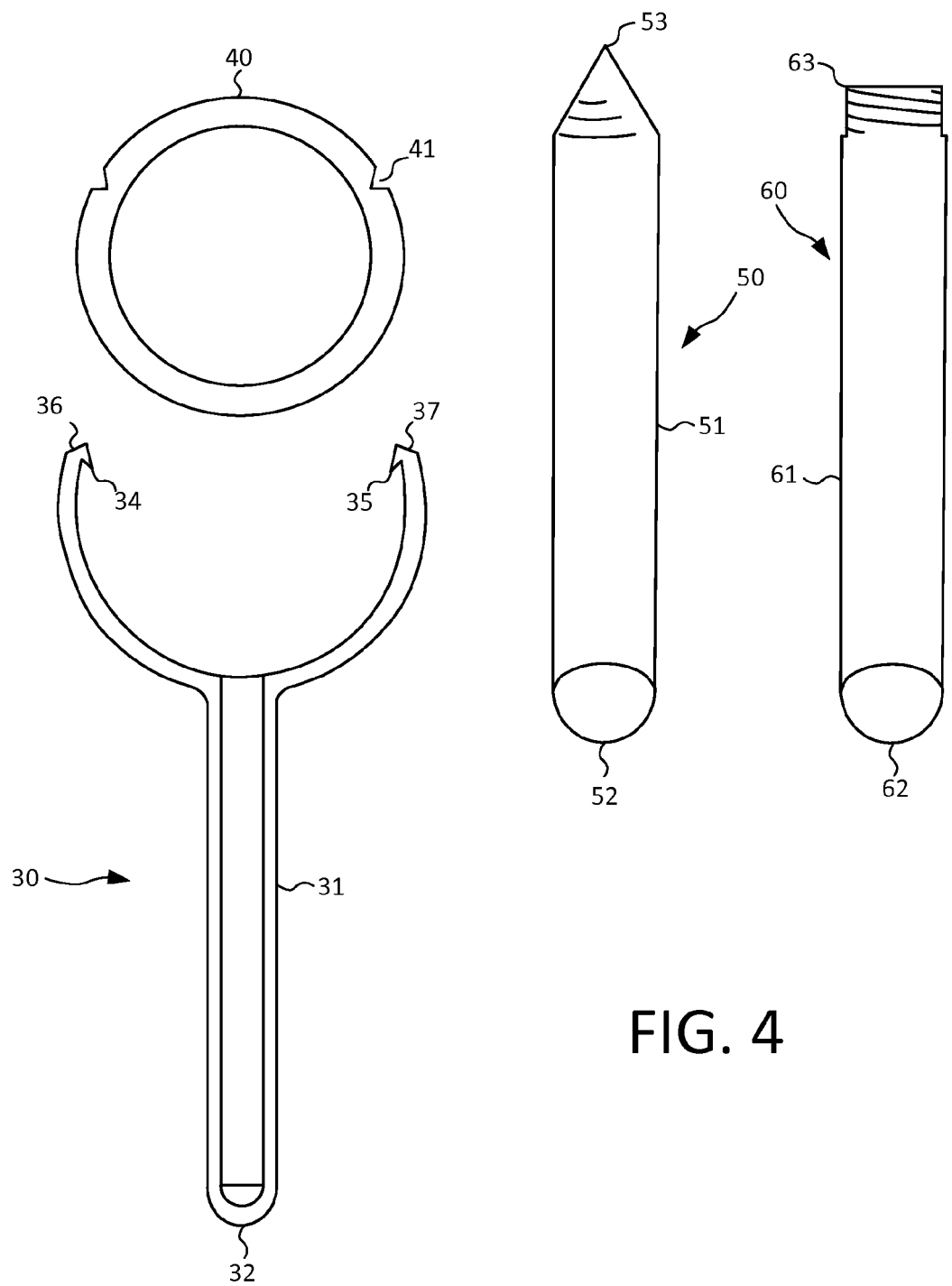
FIG. 4 is a schematic perspective view of various alternative forms of the operation portion of the devices of the present invention.

The operation portion at the distal end of the handle may comprise various configurations. For example, the operation portion may be a U-shaped collar of various designs, including but not limited to, those depicted in FIG. 1 and FIG. 4. Alternatively, the operation portion may be configured as a cone-shaped point or a threaded end piece (FIG. 4). Regardless of configuration, the operation portion will be specifically engineered to engage a particular aperture adjusting component located on a surgical headlight.

Various examples of operation portions of the present invention and their corresponding compatible aperture adjusting components include, but are not limited to, 1) an operation portion which is a U-shaped collar wherein the inside surface of the collar is engineered to comprise oval convex protrusions which engage with corresponding oval concave depressions located on the outside surface of a aperture adjusting dial (FIG. 3); 2) an operation portion which is a U-shaped collar which is engineered to comprise a beveled hook at each of its distal ends which can engage notches located on the outside surface of an aperture adjusting dial (FIG. 4); 3) an operation portion which has been engineered to comprise a cone-shaped point which can engage a compatibly-sized orifice located on the outside surface of the aperture adjusting dial (FIG. 4); and 4) an operation portion which has been engineered to comprise a threaded end which can engage a compatibly-threaded orifice located on the outside surface of the aperture adjusting dial (FIG. 4). In both example 1) and 2), the distance between the two distal ends of the U-shaped collar is slightly smaller than the outside diameter of the aperture adjusting dial. The U-shaped collar is able to engage the aperture dial using friction because it is made of a material which can temporarily expand to encompass the aperture adjusting dial and then contract back to its original shape.

Figure 5:
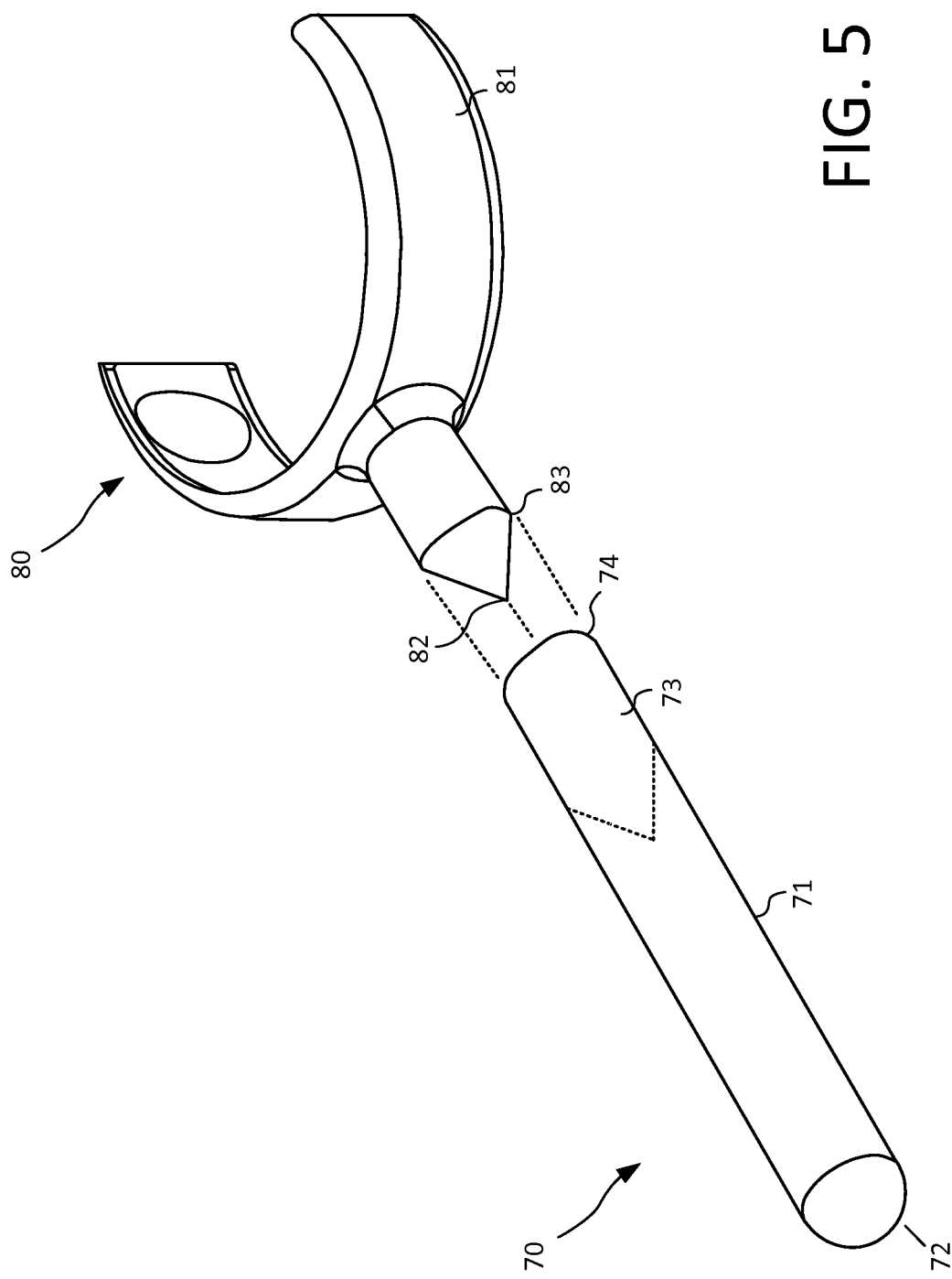
FIG. 5 is a schematic perspective view of an aperture adjusting device of the invention wherein the device is provided as a two piece unit.

In an alternative embodiment, the medical device of the present invention can be manufactured as a two-piece kit wherein the handle and operation portion are separate pieces specifically engineered to engage with one another in a manner that is generally known in the art. For example, the sterile handle may be rod-shaped and be engineered to comprise an orifice at its distal end. The separate operation portion piece will be a U-shaped collar specifically engineered to engage the outside surface of an aperture adjusting dial located on a surgical headlight (in a manner described above) and further engineered to comprise a cone-shaped point centrally located and protruding from its outside surface at its proximate end (FIG. 5). The cone-shaped point of the operation portion is capable of engaging the orifice located at the distal end of the sterile handle using friction (FIG. 5). To use this two-piece kit, the U-shaped collar is first manually engaged with the aperture adjusting dial on the surgical headlight assembly via friction prior to surgery outside the sterile field. The sterile handle is removed from its sterile packaging by a medical professional or surgeons assistant while in the sterile field and engaged with the U-shaped collar by the surgeon by inserting the cone-shaped point protruding from the outside surface of the operation portion into the orifice located at the distal end of the sterile handle using friction. The sterile handle is then used to manipulate the aperture adjusting dial to adjust the aperture of the light beam being projected from the surgical headlight assembly. After surgery, the sterile handle is removed by the surgeon (or other personnel) and properly discarded as medical waste. The U-shaped collar remains attached to the aperture adjusting dial of the surgical headlight assembly and can used in future procedures with a new sterile handle. In an alternative embodiment, the sterile handle and operation portion are engineered to be threadably engaged as described above.

The sterile one-piece aperture adjusting device and/or sterile handle of the two-piece unit are packaged in sterile peel packs or other industry standard sterile packaging readily available to those of ordinary skill in the art.

Figure 1:
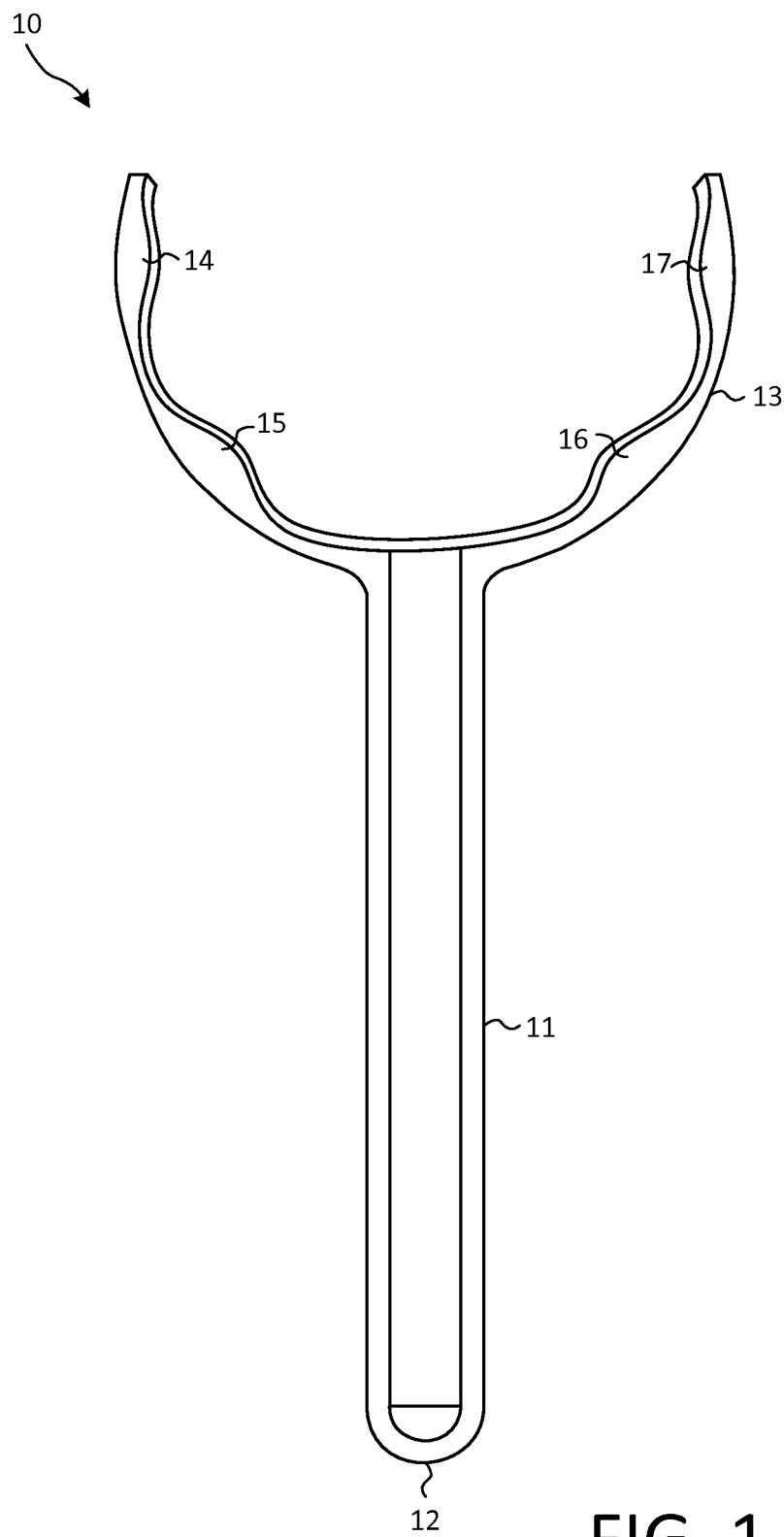
FIG. 1 is a full sectional view of one aperture adjusting device embodying the features of the present invention.

In FIG. 1 there is illustrated a top sectional view of a sterile, single-use, disposable aperture adjusting device 10 which comprises a rod-shaped handle 11 having a proximate end 12 and comprising a U-shaped collar 13 at its distal end. The inside surface of the U-shaped collar 13 is specifically engineered to comprise precisely placed oval convex protrusions 14, 15, 16 and 17.

Figure 2:
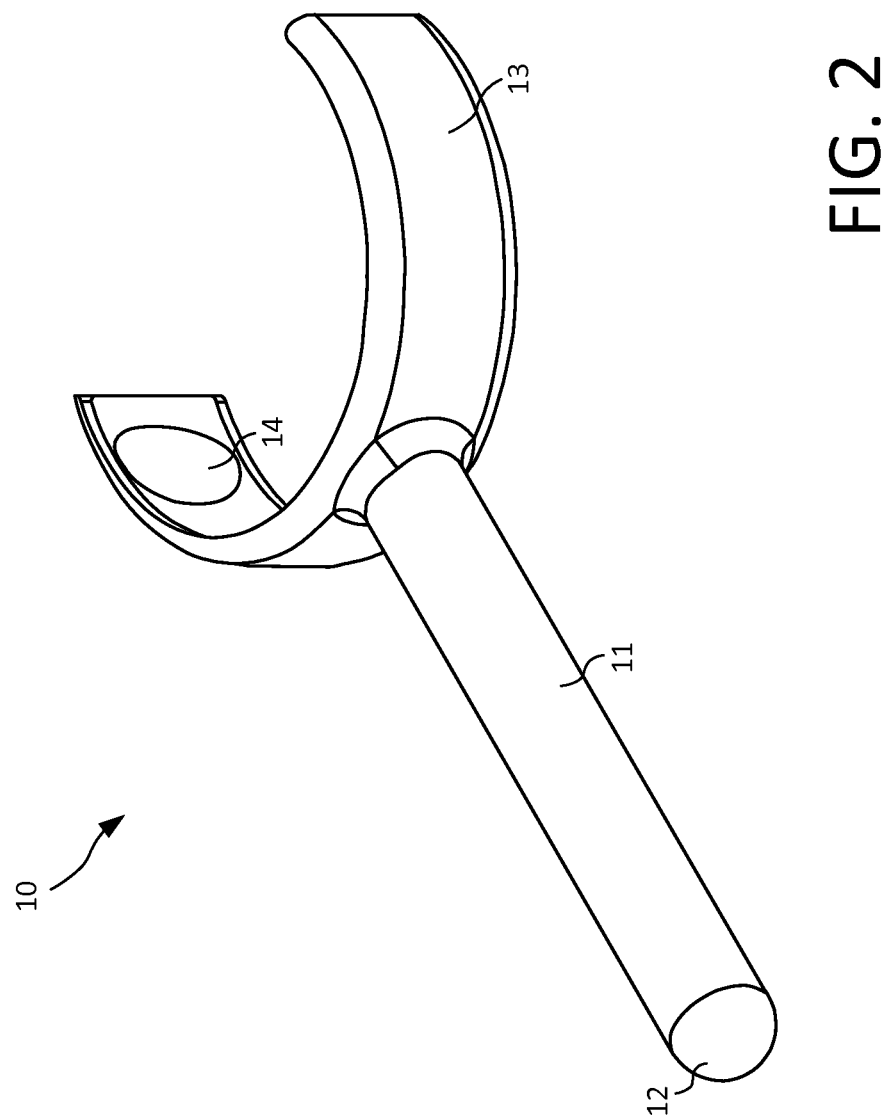
FIG. 2 is a schematic perspective view of one aperture adjusting device embodying the features of the present invention.

FIG. 2 provides a schematic perspective view of an aperture adjusting device 10 of FIG. 1 comprising a rod-shaped handle 11 having a proximate end 12 and comprising a U-shaped collar 13 at its distal end. An oval convex protrusion 14 which is one of four such protrusions engineered into the inside surface of the U-shaped collar 13 is depicted.

Figure 3:
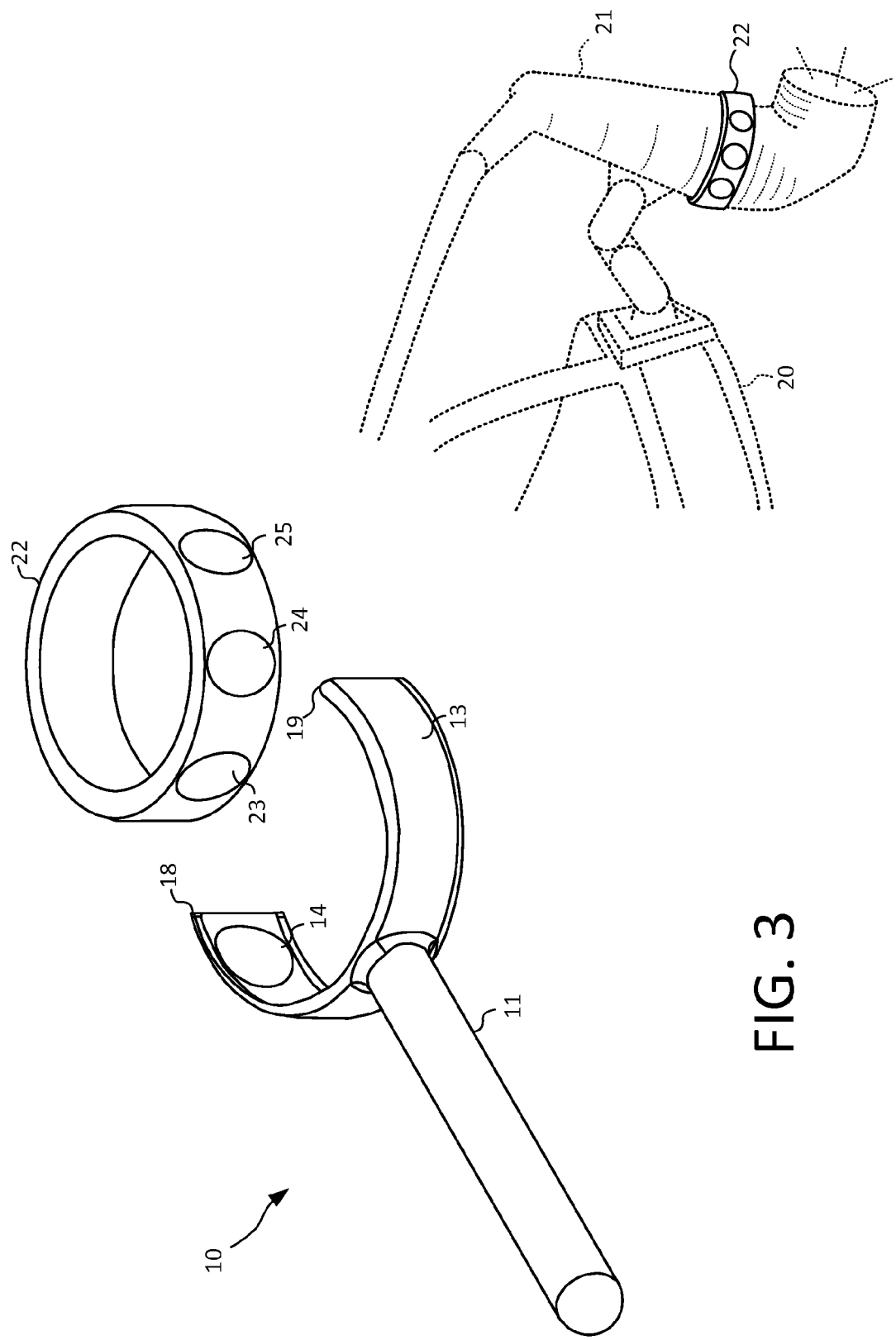
FIG. 3 is a schematic perspective view of an aperture adjusting device of the invention, a surgical headlight assembly which comprises an aperture dial, and the aperture dial assembly removed from the headlight system. The example exemplifies one embodiment of the present invention.

FIG. 3 provides a schematic perspective view of an aperture adjusting device 10 of FIG. 2, a surgical headgear 20 comprising a surgical headlight assembly 21 which comprises an aperture adjusting component in the form of an aperture adjusting dial 22, and the aperture adjusting dial 22 removed from the headlight assembly 21. The aperture adjusting dial 22 comprises a series of oval concave depressions, e.g., 23, 24 and 25. When used in the operating room, a medical professional or surgeons assistant removes the device 10 from its sterile packaging in the sterile field and the surgeon uses the handle 11 of the device 10 to engage the U-shaped collar 13 with the aperture adjusting dial 22. Specifically, the distal ends 18 and 19 of the U-shaped collar 13 temporarily expand to encompass the aperture adjusting dial 22 and then contract back to its original shape so as to engage the aperture adjusting dial 22 using friction via the engagement of the oval convex protrusions, e.g., 14, on the inside surface of the U-shaped collar 16 with the oval concave depressions, e.g., 23 on the outside surface of aperture adjusting dial 22. The surgeon then uses the handle 11 to manipulate the aperture adjusting dial 22 to adjust the aperture of the light beam being projected from the surgical headlight assembly 21.

FIGS. 4A-4C provide a schematic perspective view of various alternative forms of the operation portion of the devices of the present invention. FIG. 4A depicts a sterile, single-use, disposable aperture adjusting device 30 which comprises a rod-shaped handle 31 having a proximate end 32 and comprising a U-shaped collar 33 engineered to comprise a beveled hook 34 and 35 at each of its distal ends 36 and 37 which can engage notches, e.g., 41 located on the outside surface of an aperture adjusting dial 40. FIG. 4B depicts a sterile, single-use, disposable aperture adjusting device 50 which comprises a rod-shaped handle 51 having a proximate end 52 and which has been engineered to comprise a cone-shaped point 53 which can engage a compatibly-sized orifice located on the outside surface of the aperture adjusting dial (not shown). FIG. 4C depicts a sterile, single-use, disposable aperture adjusting device 60 which comprises a rod-shaped handle 61 having a proximate end 62 and which has been engineered to comprise a threaded end 63 which can engage a compatibly-threaded orifice located on the outside surface of the aperture adjusting dial (not shown).

FIG. 5 is a schematic perspective view of an aperture adjusting device of the invention wherein the device is provided as a two piece unit. Depicted is a sterile, single-use, disposable device 70 comprising a rod-shaped handle 71 having a proximate end 72 and engineered to comprise an orifice 73 at its distal end 74. Also depicted is a separate operation portion 80 comprising a U-shaped collar 81 specifically engineered to engage the outside surface of an aperture adjusting dial located on a surgical headlight (in a manner described above) and further engineered to comprise a cone-shaped point 82 centrally located and protruding from its outside surface at its proximate end 83. The cone-shaped point 82 of the operation portion 80 is capable of engaging the orifice 73 located at the distal end 74 of the sterile handle 71 using friction.

As apparent from the foregoing specification, the invention is susceptible of being embodied with various alterations and modifications which may differ from those described and exemplified in the preceding specification and description. It should be noted that the inventor wishes to embody within the scope of the patent warranted hereon all such modifications as reasonably and properly come within the scope of the teachings.

What is claimed is:

1. A medical device, comprising a sterile aperture adjusting device comprising a handle having a proximate end and an operation portion at its distal end; wherein said operation portion is engineered to engage the surface of an aperture adjusting component positioned on a surgical headlight assembly; wherein said aperture adjusting device is snap fit onto said aperture adjusting component and then held in place by friction fit; wherein engagement of said aperture adjusting device to said aperture adjusting component allows a user to use said handle to manipulate said aperture adjusting component to adjust the aperture of the light beam being projected from said headlight during surgery, without compromising the sterile field.

2. A medical device of claim 1, wherein said aperture adjusting component comprises an aperture adjusting dial and wherein said operation portion comprises a U-shaped collar; wherein said U-shaped collar is specifically engineered to engage said aperture adjusting dial.

3. A medical device of claim 2, wherein the inside surface of said U-shaped collar comprises a series of oval convex protrusions capable of engaging with a series of oval concave depressions located on the outside surface of said aperture adjusting dial.

4. A method of adjusting the aperture of the light beam being projected from a surgical headlight assembly secured to the head of a surgeon during surgery; comprising the steps of: removal of a sterile aperture adjusting device of claim 1 from its packaging by a medical professional or surgeons assistant in the sterile field; use of the handle of said aperture adjusting device by the surgeon to engage said device to an aperture adjusting component positioned on said surgical headlight assembly; wherein said aperture adjusting device is snap fit onto said aperture adjusting component and then held in place by friction fit; and use of said handle by the surgeon to manipulate said adjusting component to adjust the aperture of said projected light beam during the surgical procedure, without compromising the sterile field.

\* \* \* \* \*